US010226571B2

(12) United States Patent
Davis et al.

(10) Patent No.: US 10,226,571 B2
(45) Date of Patent: Mar. 12, 2019

(54) PUMP SEGMENT PLACEMENT

(71) Applicant: CareFusion 303, Inc., San Diego, CA (US)

(72) Inventors: Lisa Davis, San Diego, CA (US); Robert Butterfield, San Diego, CA (US); Chris Zollinger, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 451 days.

(21) Appl. No.: 13/827,775

(22) Filed: Mar. 14, 2013

(65) Prior Publication Data
US 2014/0276424 A1 Sep. 18, 2014

(51) Int. Cl.
*F04B 43/08* (2006.01)
*A61M 5/142* (2006.01)
*F04B 43/12* (2006.01)
*A61J 1/10* (2006.01)
*A61J 1/20* (2006.01)
*A61M 39/28* (2006.01)

(52) U.S. Cl.
CPC ......... *A61M 5/14228* (2013.01); *F04B 43/08* (2013.01); *F04B 43/12* (2013.01); *F04B 43/1253* (2013.01); *A61J 1/10* (2013.01); *A61J 1/2037* (2015.05); *A61M 39/281* (2013.01); *A61M 2205/121* (2013.01); *A61M 2205/128* (2013.01); *A61M 2205/14* (2013.01); *A61M 2205/581* (2013.01); *A61M 2205/582* (2013.01); *A61M 2205/583* (2013.01); *A61M 2205/6045* (2013.01); *A61M 2205/6081* (2013.01)

(58) Field of Classification Search
CPC ...... F04B 43/08; F04B 43/12; F04B 43/1253; A61M 5/14212; A61M 5/24224; A61M 2205/12; A61M 5/1406; A61M 5/142; A61M 5/14216; A61M 5/14228
USPC ............................................ 417/477.2, 477.9
See application file for complete search history.

(56) References Cited

U.S. PATENT DOCUMENTS

| | | | |
|---|---|---|---|
| 4,559,040 A | 12/1985 | Horres et al. | |
| 4,605,396 A | 8/1986 | Tseo et al. | |
| 4,741,736 A | 5/1988 | Brown | |
| 4,756,706 A | 7/1988 | Kerns et al. | |
| 4,850,980 A | 7/1989 | Lentz et al. | |
| 4,898,578 A | 2/1990 | Rubalcaba, Jr. | |
| 5,213,483 A | 5/1993 | Flaherty et al. | |

(Continued)

FOREIGN PATENT DOCUMENTS

| | | |
|---|---|---|
| EP | 1684396 A2 | 7/2006 |
| EP | 2560116 A2 | 2/2013 |

(Continued)

*Primary Examiner* — Philip E Stimpert
(74) *Attorney, Agent, or Firm* — Mintz Levin Cohn Ferris Glovsky and Popeo, P.C.

(57) ABSTRACT

A pump cassette is configured for coupling with a pump device. The pump cassette may include a fluid lumen adapted for passage and propulsion of an infusion fluid toward a patient; a valve assembly that can be actuated to regulate fluid flow through the fluid lumen; and a frame coupled to the fluid lumen and the valve assembly. The frame is adapted to be inserted into a seat of a pump device. The frame is configured to be inserted into the seat only when aligned in a predetermined orientation relative to the seat.

16 Claims, 9 Drawing Sheets

(56) References Cited

U.S. PATENT DOCUMENTS

| | | | |
|---|---|---|---|
| 5,370,510 A * | 12/1994 | Sinclair | F04B 43/1223 417/477.14 |
| 5,482,446 A | 1/1996 | Williamson et al. | |
| 5,575,632 A | 11/1996 | Morris et al. | |
| 5,658,252 A | 8/1997 | Johnson | |
| 5,782,805 A | 7/1998 | Meinzer et al. | |
| 5,954,527 A | 9/1999 | Jhuboo et al. | |
| 6,056,522 A | 5/2000 | Johnson | |
| 6,123,686 A | 9/2000 | Olsen et al. | |
| 6,165,149 A * | 12/2000 | Utterberg et al. | 604/5.01 |
| 6,593,528 B2 | 7/2003 | Franklin-Lees et al. | |
| 6,752,787 B1 | 6/2004 | Causey, III et al. | |
| 6,942,473 B2 | 9/2005 | Abrahamson et al. | |
| 7,150,735 B2 | 12/2006 | Hickle | |
| 7,316,648 B2 | 1/2008 | Kelly et al. | |
| 7,553,291 B2 | 6/2009 | Duffy et al. | |
| 7,662,139 B2 | 2/2010 | Demers et al. | |
| 7,713,240 B2 | 5/2010 | Istoc et al. | |
| 7,884,735 B2 | 2/2011 | Newkirk | |
| 7,933,780 B2 | 4/2011 | De La Huerga | |
| 7,978,564 B2 | 7/2011 | De La Huerga | |
| 8,057,437 B2 | 11/2011 | Ziegler | |
| 8,118,778 B2 | 2/2012 | Haylor et al. | |
| 8,224,481 B2 | 7/2012 | Bylsma et al. | |
| 8,310,468 B2 | 11/2012 | Martin | |
| 8,328,758 B2 | 12/2012 | Childers et al. | |
| 8,353,288 B2 | 1/2013 | Schermeier et al. | |
| 2002/0147425 A1 * | 10/2002 | Briggs | F04B 43/08 604/65 |
| 2002/0165503 A1 | 11/2002 | Morris et al. | |
| 2004/0019313 A1 | 1/2004 | Childers et al. | |
| 2005/0033124 A1 | 2/2005 | Kelly et al. | |
| 2005/0267439 A1 | 12/2005 | Harr et al. | |
| 2005/0277890 A1 | 12/2005 | Stewart et al. | |
| 2006/0241356 A1 | 10/2006 | Flaherty | |
| 2007/0156089 A1 * | 7/2007 | Yu | A61M 5/14232 604/131 |
| 2007/0219495 A1 | 9/2007 | Kato et al. | |
| 2008/0045904 A1 | 2/2008 | Estes et al. | |
| 2008/0079392 A1 | 4/2008 | Baarman et al. | |
| 2008/0269716 A1 | 10/2008 | Bonde et al. | |
| 2008/0287763 A1 | 11/2008 | Hayter | |
| 2009/0106567 A1 | 4/2009 | Baarman | |
| 2009/0115199 A1 * | 5/2009 | Dale | 292/303 |
| 2009/0221964 A1 | 9/2009 | Rotem et al. | |
| 2009/0306592 A1 | 12/2009 | Kasai et al. | |
| 2010/0319796 A1 * | 12/2010 | Whitaker | F16K 11/085 137/625.46 |
| 2011/0004143 A1 | 1/2011 | Beiriger et al. | |
| 2011/0178462 A1 | 7/2011 | Moberg et al. | |
| 2012/0035581 A1 | 2/2012 | Travis | |
| 2012/0078218 A1 | 3/2012 | Barnes | |
| 2012/0179130 A1 | 7/2012 | Barnes et al. | |
| 2012/0191059 A1 * | 7/2012 | Cummings et al. | 604/500 |
| 2012/0266965 A1 | 10/2012 | Hariharesan et al. | |
| 2012/0312196 A1 | 12/2012 | Newkirk | |
| 2013/0046871 A1 | 2/2013 | Vik et al. | |
| 2013/0092728 A1 | 4/2013 | Vik et al. | |
| 2014/0265611 A1 | 9/2014 | Fern et al. | |
| 2014/0271246 A1 | 9/2014 | Zollinger et al. | |
| 2014/0271247 A1 | 9/2014 | Abal | |
| 2014/0276425 A1 | 9/2014 | Zollinger et al. | |
| 2014/0276426 A1 | 9/2014 | Borges et al. | |
| 2014/0276533 A1 | 9/2014 | Butterfield et al. | |

FOREIGN PATENT DOCUMENTS

| | | |
|---|---|---|
| JP | 2001-0187136 A | 7/2001 |
| RU | 2336906 C2 | 10/2008 |
| RU | 2437168 C2 | 12/2011 |
| WO | WO-96-27402 A1 | 9/1996 |
| WO | WO-2005050524 A2 | 6/2005 |
| WO | WO-2008/017041 A2 | 2/2008 |
| WO | WO-2012007942 A2 | 1/2012 |

* cited by examiner

PUMP SEGMENT PLACEMENT

BACKGROUND

Infusion pump and sensing device systems are widely used in the medical field for infusing a fluid, such as a medication, to a patient in the environment of intensive care units, cardiac care units, operating rooms or trauma centers. Several types of infusion pump systems permit the infusion of several medications using pumps that are modularly coupled to one another, as it may often be necessary to simultaneously infuse into the patient several different kinds of fluids. Some of the several types of fluids, such as drugs, may not be directly compatible with each other and therefore need to be infused into the patient at different points of the body or at different times.

In this regard, there exist modular systems in which pump and monitoring modules can be selectively attached, both physically and electrically, to a central management unit. The central management unit controls the operation of pump modules attached to it, and receives and displays information regarding the pump modules. Each module may include a modular pump that is configured to be removably coupled to a corresponding pump cassette that enables the pumping of fluid. It is important that the proper pump cassette be coupled to the proper module pump device as certain pump devices and pump cassettes are configured to only pump a certain type of fluid, such as a type of drug. It is also important that the pump cassette be properly inserted or coupled to the modular pump.

In view of the foregoing, there is a need for infusion pump systems that facilitate the proper coupling of a pump cassette to the proper modular pump device.

SUMMARY

Disclosed is a pump cassette for coupling with a pump device, the pump cassette comprising: a fluid lumen adapted for passage and propulsion of an infusion fluid toward a patient; a valve assembly that can be actuated to regulate fluid flow through the fluid lumen; and a frame coupled to the fluid lumen and the valve assembly, the frame adapted to be inserted into a seat of a pump device, the frame configured to be inserted into the seat only when aligned in a predetermined orientation relative to the seat.

Further disclosed is a pump device, comprising: a pumping mechanism; a housing defining a seat configured to receive a pump cassette having a fluid lumen that can be acted upon by the pumping mechanism so as to pump fluid through the fluid lumen of the pump cassette, wherein the valve assembly transitions between a flow state that permits fluid flow through the fluid lumen and a non-flow state that blocks fluid flow through the fluid lumen, the seat shaped to receive a pump cassette only when the pump cassette is aligned in a predetermined orientation relative to the seat; a door attached to the housing and configured to be transitioned between an open position wherein the seat is exposed for receipt of a pump cassette and a closed position wherein the door secures a pump cassette within the seat; and a door actuator configured to transition to a locked state that locks the door in the closed position, wherein the door actuator is configured to automatically transition the valve assembly to the open state when the door actuator is transitioned to the locked state.

Further disclosed is a method for coupling a pump cassette with an infusion pump, the method comprising: aligning a pump cassette in a predetermined orientation relative to the infusion pump, wherein the pump cassette can only be coupled to the infusion pump when the pump cassette is aligned in the predetermined orientation relative to the infusion pump; and inserting at least a portion of the pump cassette into the infusion pump.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

Like reference symbols in the various drawings indicate like elements.

DETAILED DESCRIPTION

Disclosed is a medical fluid infusion system configured for pumping a fluid to a patient, such as in a hospital environment. The system includes one or more modular pump devices each of which is configured to be removably coupled to a pump cassette. When coupled to one another, the modular pump device and pump cassette can collectively pump a fluid to a patient. The pump cassette is configured to be coupled to the modular pump device such as by inserting the pump cassette into a seat of the pump device. The pump cassette is sized and shaped to be inserted into the modular pump device only when the pump cassette is aligned in a predetermined orientation relative to the modular pump device. This ensures that the pump cassette will be properly inserted into the modular pump device so as to eliminate or reduce the likelihood of improper pump operation.

In addition, the pump cassette may be particularly adapted for coupling only to a particular type of modular pump device. For example, the pump cassette may be adapted to be coupled only to a modular pump device having a particular type of pumping mechanism (such as a peristaltic pump) or to a pump that pumps a particular type of fluid, such as a particular type of drug.

For such circumstances, an identifier may be associated with the pump cassette wherein the identifier matches with a corresponding or complementary identifier on the proper type of modular pump device to which the pump cassette matches. The identifier may be any type of identifier that uniquely identifies the pump cassette and that can be associated with a corresponding identifier on the modular pump device. For example, the identifier may be a color code on the pump cassette that is identical to or otherwise matches with a corresponding color code on the modular pump device. Any type of identifier may be used, such as, for example, a symbol, sound, or color.

Figure 1:
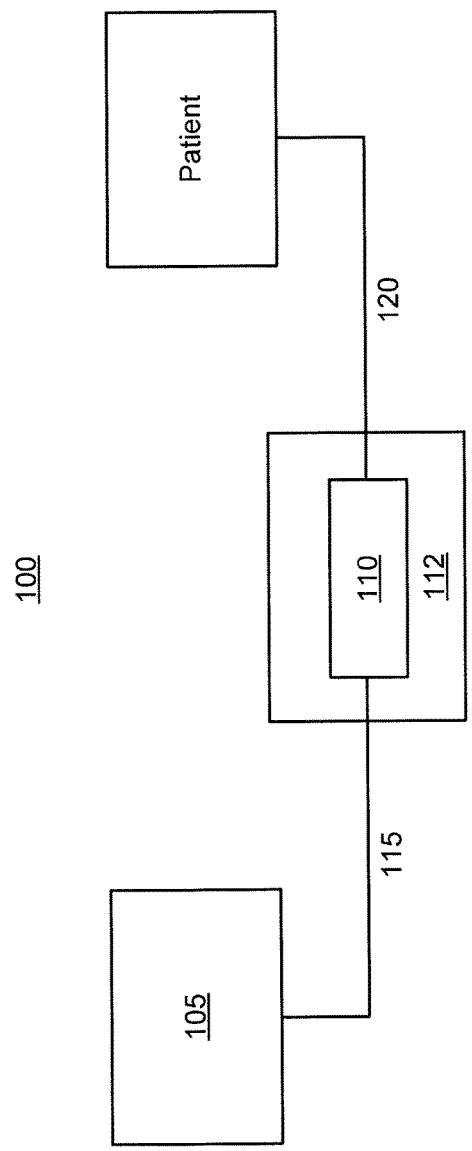
FIG. 1 shows a schematic view an infusion system configured for pumping a fluid to a patient.

FIG. 1 shows a schematic representation of an infusion system 100 configured to be used in pumping a fluid to a patient. The infusion system 100 includes a fluid container, such as an intravenous (IV) bag 105, fluidly coupled to a pump cassette 110 via a fluid conduit, such as a tube 115. The pump cassette 110 is configured to pump fluid from the IV bag 105 toward a patient via a tube 120 when the pump cassette 110 is coupled to a modular pump device 112. The pump cassette 110 is configured to be removably coupled to the modular pump device 112 such as by inserting the pump cassette 112 into a seat of the modular pump device 112. The following U.S. patent application describes an exemplary pump system and is incorporated by reference herein in its entirety: U.S. patent application Ser. No. 13/829,744 entitled "Inductively Powered Modular Medical Device System", filed concurrently herewith.

With reference still to FIG. 1, the tube 115 has a proximal end fluidly coupled to (such as via a drip chamber) the IV bag 105, and a distal end fluidly coupled to a fluid lumen 205 (FIG. 2) of the pump cassette 110. Likewise, the tube 120 has a proximal end fluidly coupled to a fluid lumen of the pump cassette 110 and a distal end that attaches to the patient via an IV connection. Either of the tubes 115 or 120 may be formed of a single tube or may be formed of a series of tubes removably attached to one another, such as in an end-to-end manner using any of a variety of connectors such as Luer connectors. The tubes 115 and 120 and the fluid lumen 205 (FIG. 2) of the pump cassette 110 collectively form a continuous fluid lumen that provides a fluid pathway from the IV bag 105 toward the patient. The combinations of components 115 (with drip chamber), 110 and 120 (with luer fitting) comprise what is termed an "IV set". This continuous fluid lumen may include any of a variety of components that facilitate or otherwise are used in connecting the tubes and/or pumping fluid, including, for example, valves, filters, free-flow stop valves, pressure and air detection regions or components and access connectors, etc. Any of a variety of additional components may be used, including, for example, anti-free flow devices, pressure sensing components, air detection components, etc.

Figure 2:
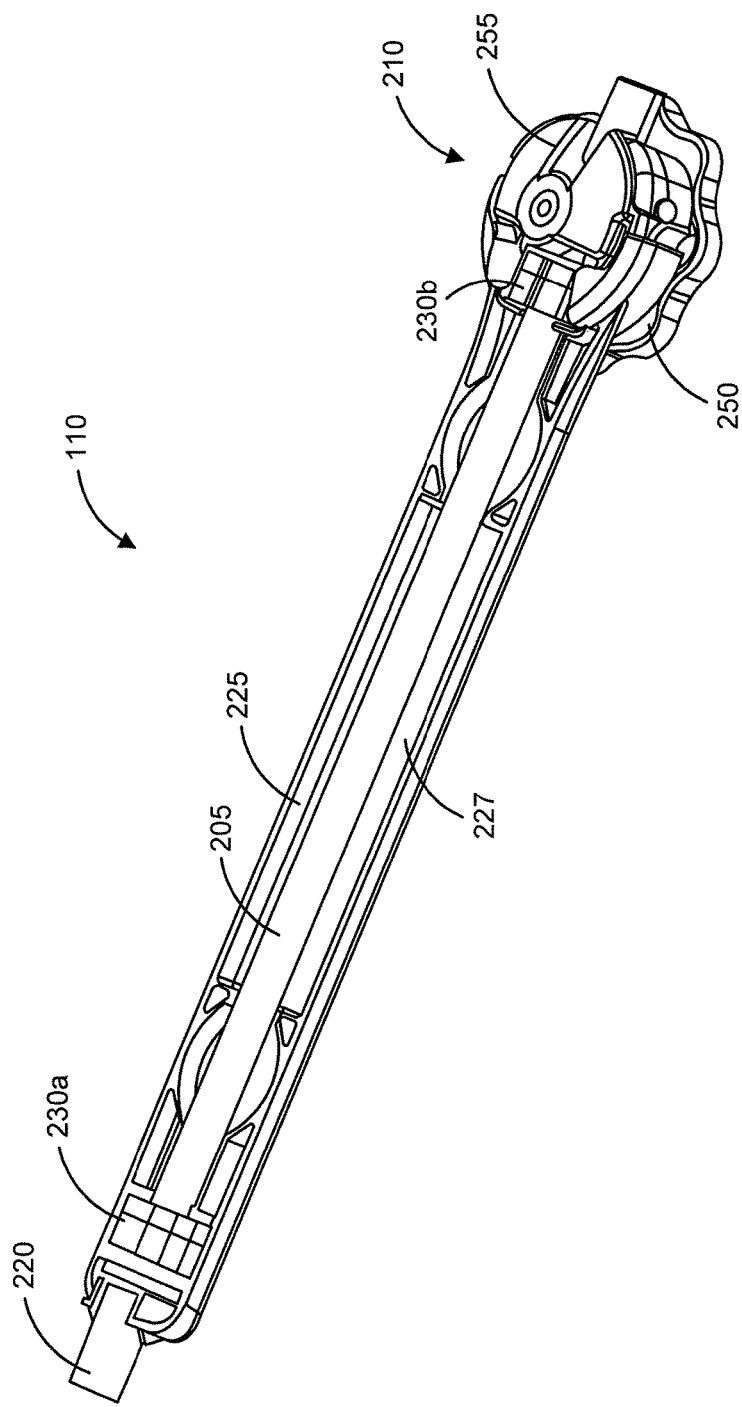
FIGS. 2 and 3 shows perspective views of an exemplary pump cassette for use with the system of FIG. 1.
Figure 3:
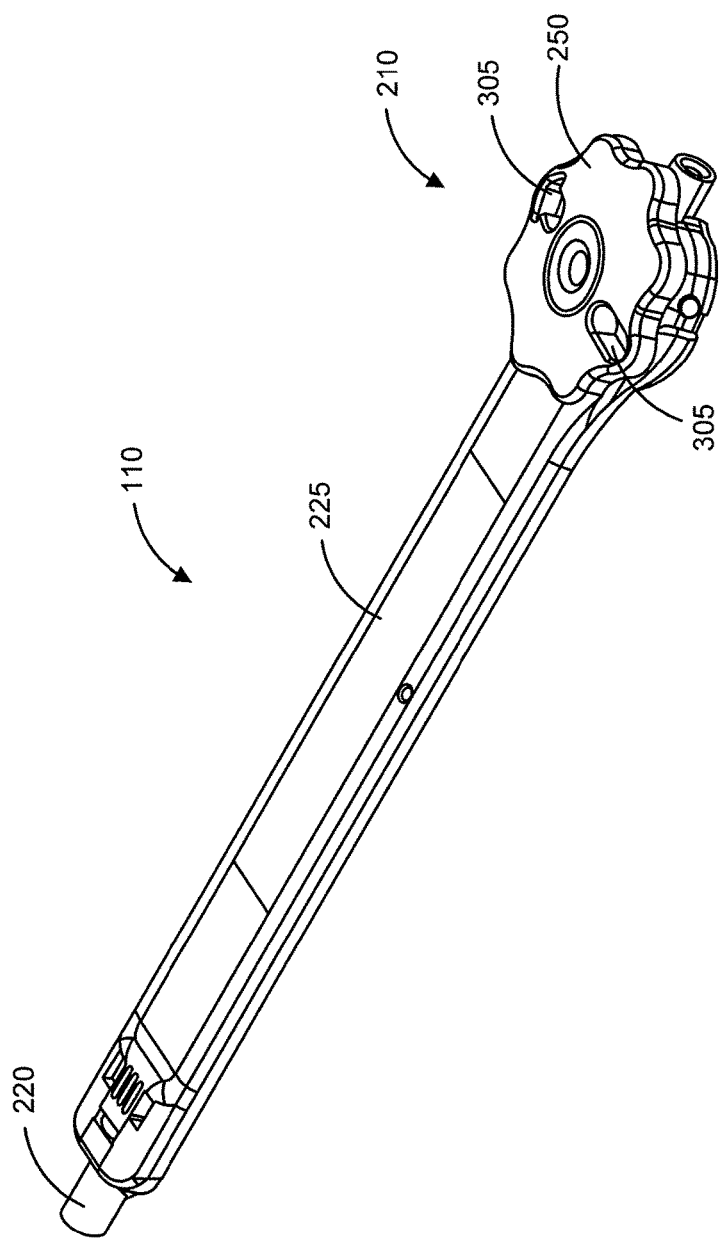
Figure 4:
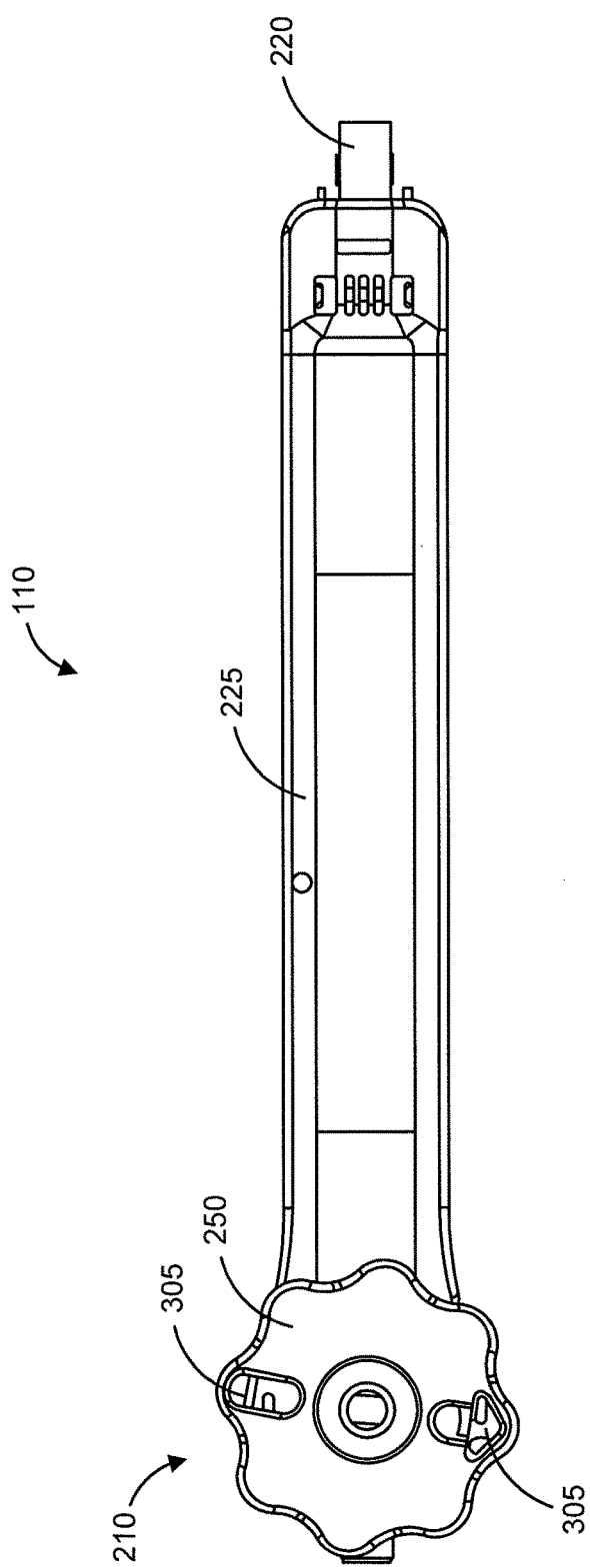
FIGS. 4 and 5 show top and bottom plan views, respectively, of the pump cassette.
Figure 5:
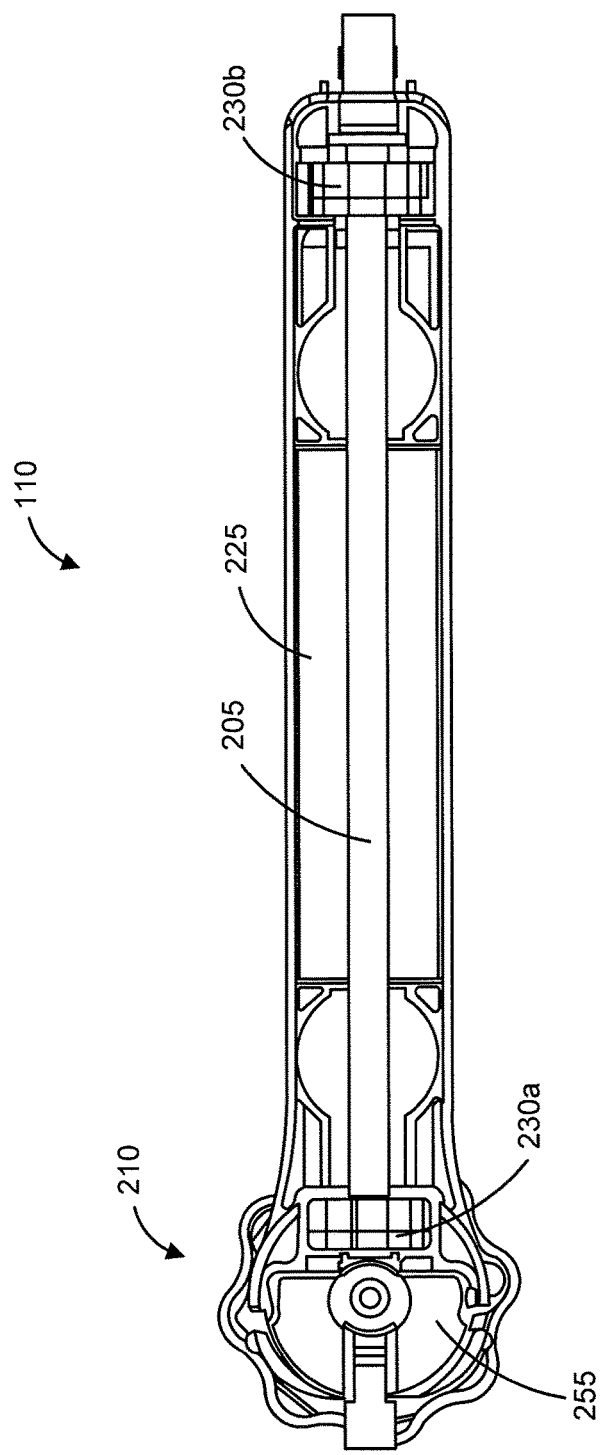

FIGS. 2 and 3 shows perspective views of an exemplary pump cassette 110. FIGS. 4 and 5 show top and bottom plan views, respectively, of the pump cassette 110. As mentioned, the pump cassette 110 may be in the form of an assembly that removably inserts into a modular pump device. With reference to FIG. 2, the pump cassette 110 includes a fluid lumen 205. When the pump cassette 110 is attached to the tubes 115 and 120, the fluid lumen 205 fluidly connects the tube 115 to the tube 120. The fluid lumen 205 may be acted upon by any of a variety of pump mechanisms of the modular pump device to pump fluid through the fluid lumen 205 in order to achieve fluid flow from the IV bag 105 to or toward the patient.

As mentioned, the pump cassette 110 may be particularly adapted for coupling only to a particular type of modular pump device. For example, the pump cassette may be adapted to be coupled only to a modular pump device having a particular type of pumping mechanism (such as a peristaltic pump) or to a pump that pumps a particular type of fluid, such as a particular type of drug.

For such circumstances, an identifier may be associated with the pump cassette wherein the identifier matches with a corresponding or complementary identifier on the particular modular pump device to which the pump cassette matches. The identifier may be any type of identifier that uniquely identifies the pump cassette and that can be associated with a corresponding identifier on the modular pump device. For example, the identifier may be a color code on the pump cassette that is identical to or otherwise matches with a corresponding color code on the modular pump device. Any type of identifier may be used, such as, for example, a symbol, sound, or color. The identifier may be used to, for example, to facilitate quick and accurate installation of the pump cassette into the device.

Any of a variety of structures may be used to form the fluid lumen 205 of the pump cassette 110. For example, with reference to FIGS. 2 and 5, the fluid lumen 205 may be formed of a tubular structure that defines the fluid lumen 205. The tubular structure may be formed of any of a variety of materials, including for example polysiloxane (e.g., "silicone rubber"), plasticized Polyvinyl chloride (PVC), silicone, thermoplastic elastomers, elastomeric plastics, butyl rubber, or other materials. Any of a variety of connectors and/or valves may be used to attach the fluid lumen 205 to the tubes 115 and 120.

The fluid lumen 205 has a cross-sectional shape along a plane generally normal to the direction of fluid flow through which fluid can flow. The cross-sectional shape may vary along the interior or exterior of the fluid lumen. For example, the cross-sectional shape may be circular. Or, the cross-sectional shape may be a non-circular shape that facilitates compression of the outer walls of the fluid lumen when a pump mechanism is acting on the fluid lumen. The pump mechanism may achieve pumping through the fluid lumen 205 such as by compressing and/or deforming one or more portions of the fluid lumen to achieve fluid flow through the lumen. The non-circular cross-sectional shape may be, for example, a generally flattened shape, such as oval shape, eye, or diamond shape, that facilitates further flattening of the fluid lumen when a pump mechanism acts on the fluid lumen.

A proximal end of the fluid lumen tubular structure is fluidly and mechanically attached to the tube 115, such as via a valve assembly 210. A distal end of the fluid lumen tubular structure is attached to the tube 120, such as via a connector 220. The fluid lumen 205 may also be formed of two or more structures that collectively define the fluid lumen 205 therebetween.

With reference still to FIGS. 2-5, the fluid lumen 205 is positioned on a frame 225. The frame 225 is formed of a relatively hard or rigid material such that the frame may act as a platen 227 relative to the fluid lumen 205 for pumping fluid through the fluid lumen 205. The platen 227 may be flat or curved to cooperate in the reduction of forces required to ensure adequacy of occlusion of the moving occluding elements (such as fingers) of a pump mechanism. That is, the platen 227 may be shaped so as to cooperate with or form the non-circular cross-section of the fluid lumen 205 discussed above.

The relatively rigid structure of the frame 225 can be used to secure the fluid lumen 205 in a fixed position and/or shape relative to the frame 225, such as to eliminate or reduce the risk of the fluid lumen 205 being unintentionally stretched or moved during positioning of the frame 225 into the modular pump device. Moreover, the rigid structure of the frame 225 may be used to provide a controlled degree of stretching of the fluid lumen 205 to enhance the accuracy of the achieved fluid flow rate. It should be appreciated that accidental or unintended stretching or deformation of the fluid lumen 205 may interfere with pumping accuracy as such stretching or deformation will change the flow geometry. The rigid frame 225 and the clips 230 (described below) that secure the fluid lumen 205 to the frame 225 can be used to secure the fluid lumen 225 in a predetermined, fixed geometry that is unlikely to incur undesired deformation or stretching.

As best shown in FIGS. 2 and 5, one or more attachment members, such as clips 230, are configured to secure the fluid lumen 205 to the frame 225. In the illustrated version, two clips 230a and 230b are positioned over the fluid lumen 205 and attached to the frame 225 such that the clips 230 secure the fluid lumen 205 to the frame 225. The first clip 230a is located near one end of the fluid lumen 205 and the second clip 230b is located near an opposite end of the fluid lumen 205. It should be appreciated, however, that various quantities of clips may be used at any of a variety of locations along the fluid lumen 205 and/or the frame 225. In addition, for certain materials of the fluid lumen 205 (such as thermoplastic elastomers, the fluid lumen 205 may be bonded to the connector 220 or to at least a portion of the rotary valve 210, such a connector portion of the rotary valve. For example, a solvent or adhesive can be used to secure the fluid lumen 205 to the connector 220 or to at least a portion of the rotary valve 210, such a connector portion of the rotary valve.

Figure 6:
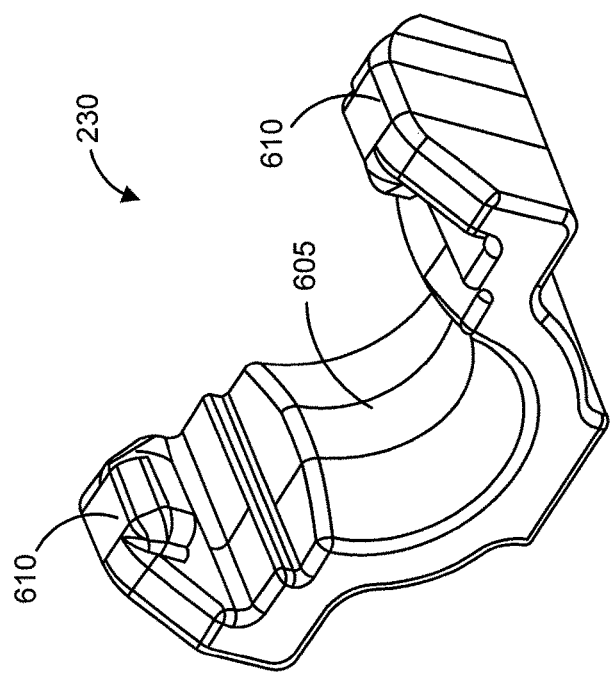
FIG. 6 shows an enlarged view of a clip for securing a fluid lumen to the pump cassette.

FIG. 6 shows an enlarged view of one of the clips 230. The clip 230 generally has c-shape that defines a seat 605 sized and shaped to receive the fluid lumen 205. The clip 230 has a pair of ends 610 that each attach to the frame 225. In this manner, the clip 230 (or clips 230) secures the fluid lumen 205 to the frame 225. It should be appreciated that the clips 230 may have a variety of shapes and/or structures and that the version show in FIG. 6 is a non-limiting example. The seat 605 may define a shape, such as a non-circular shape that corresponds to a desired or predetermined shape of the fluid lumen 205. In this manner, the clips 230 may be used to secure the fluid lumen 205 in its desired shape. Other portions or components may also define a shape that corresponds to a desired or predetermined shape of the fluid lumen 205. For example, the connector 220 or a connector portion of the rotary valve may define such shapes.

With reference again to FIGS. 2-5, the pump cassette 110 may be configured so that it can only be inserted into the modular pump device when aligned in a predetermined manner relative to the modular pump device. This eliminates or reduces the likelihood that the pump cassette 110 will be inserted in an incorrect or improper orientation into the modular pump device, which could interfere with completion of engagement by such structures as a door and which might cause damage to sensors located on the face of the instrument or to elements of the pump cassette. In this regard, the pump cassette 110 may be shaped so that it can only be inserted into the modular pump device when positioned in a predetermined orientation relative to the modular pump device. For example, the frame 225 can have an asymmetric shape that fits into a complementary-shaped seat in the modular pump device housing. Or the frame 225 can have one or more prongs or protrusions that must be aligned with complementary-shaped seats in the modular pump device in order for the frame 225 to be inserted into the modular pump device.

In the version of FIGS. 2-5, the frame 225 has shape that is asymmetric about a vertical axis. The frame 225 has a head region that is rounded and enlarged relative to a relatively thinner elongated body region. This provides the frame 225 with a key-like shape that can only be inserted into a complementary-shaped seat in the modular pump device housing when the frame 225 and the modular pump device housing are properly aligned. Any of a variety of asymmetric shapes can be used. Such asymmetric shape should complement or be identical to a seat in the modular pump device so that the pump cassette fits in the seat only when properly aligned relative to the seat. The manner in which the frame 225 inserts into the seat of the modular pump is described in more detail below with reference to FIGS. 7-10.

The pump cassette 110 includes a valve assembly 210. The valve assembly 210 includes a valve coupled to the fluid lumen 205 for controlling fluid flow through the fluid lumen 205. The valve can function in a variety of manners relative to the fluid lumen. For example, the valve can function as a gravity flow stop in that it has a "flow" state that permits flow through the fluid lumen 205 and a "non-flow" state that stops or blocks flow through the fluid lumen 205. On installation, the valve is opened to allow pumping and on removal, closed to prevent inadvertent (and dangerous) uncontrolled gravity free flow. Or, the valve can function as a flow regulator that permits various levels of flow rate, such as variable flow resistance, through the fluid lumen 205 based upon various, corresponding states of the valve.

In the version shown in FIGS. 2-5, the valve assembly 210 comprises a rotary valve that transitions between a non-flow state and a flow state. The valve assembly 210 is located at the head region of the frame 225 where the tube 115 attaches to the fluid lumen 205, although the position of the valve assembly 210 may vary. The valve assembly 210 includes a valve handle 250 that is functionally coupled to a valve body, such as a rotary valve 255, as best shown in FIGS. 2 and 5. The valve handle 250 can be actuated to open and close the rotary valve 255. For example, the valve handle 250 can rotate between an open and a closed position. When valve handle 250 is in the open position, the valve is open to permit fluid flow through the fluid lumen 205. Likewise, when the valve handle 250 is in the closed position, the valve is closed to stop or block fluid flow through the fluid lumen 205.

With reference to FIG. 3, the valve handle 250 may have a disk-like shape in that the valve handle 250 is relatively round and planar or substantially flat. In the illustrated version, the valve handle 250 is circular with an undulating (knurled) circumference that forms a series of indentations to assist gripping. One or more coupling elements, such as slots 305, are located on the valve handle 250. As described more fully below, the slots 305 are configured to mate with complementary coupling elements, such as tabs, of the modular pump device. When properly coupled to the modular pump device, the act of coupling (or a portion thereof) causes the modular pump device to automatically transition the valve handle 250 to an open position that opens the valve body so as to permit fluid flow through the fluid lumen 205.

Figure 7:
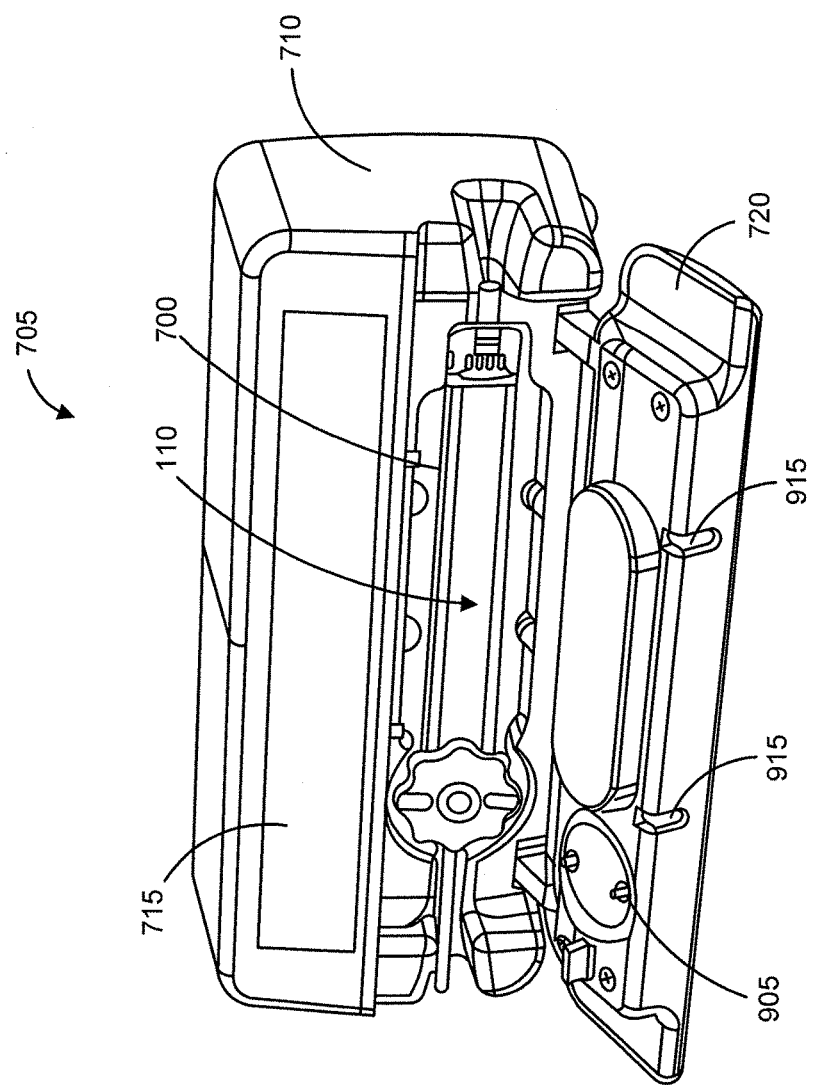
FIG. 7 shows a front view of the pump cassette mounted in a seat of a modular pump device.

FIG. 7 shows a front view of the pump cassette 110 mounted in a seat 700 of a modular pump device 705. The seat 700 has a shape that is configured to snugly receive the pump cassette 110. The seat may have one or more features, such as tabs or prongs, configured to yield when the pump cassette 110 is pushed into the seat 700 and then snap into place to secure the pump cassette 110 within the seat 700 once the pump cassette 110 is mounted therein. A feedback, such as a tactile, audio, or visual feedback, may be provided when the pump cassette 110 is securely mounted in the seat 700. For example, a snapping sound may occur when the pump cassette 110 is securely mounted in the seat.

With reference still to FIG. 7, the modular pump device 705 is formed of an outer housing 710 having a front panel 715 on which a user interface or display panel may be positioned. The housing 710 defines an internal cavity in which is mounted a pump mechanism that is configured to act on the fluid lumen 205 (FIG. 2) of the pump cassette 110 for pumping fluid through the fluid lumen 205. Any type of pump mechanism may be used, including a peristaltic pump mechanism.

In the example shown in FIG. 7, the seat 700 is positioned adjacent the front panel 715 although the relative positions may vary. The modular pump device 705 includes an access element, such as an access door 720, that can be opened to access and expose a seat where the pump cassette 110 can be inserted into the pump. The access door 720 is movably attached to the housing 710 such as via a hinge assembly that permits the door 720 to transition between an open state (as shown in FIG. 7) and a closed state (as shown in FIG. 8.)

Figure 8:
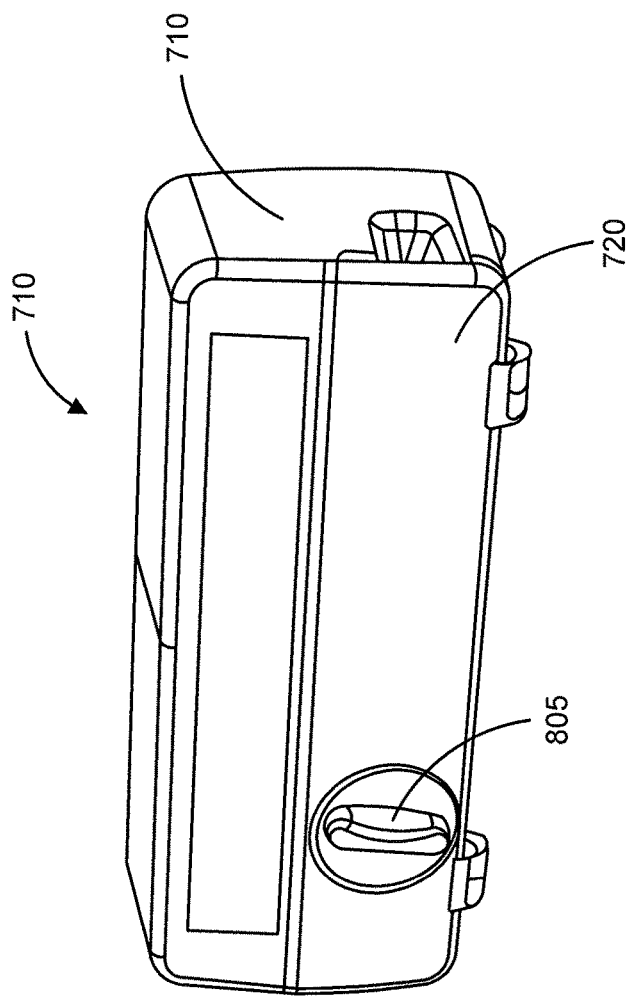
FIG. 8 shows the modular pump device with a door in a closed state.

As best shown in FIG. 8, an actuator, such as knob 805, is coupled to the door 720. The knob 805 can be actuated by a user to lock the door 720 once the door is closed with the pump cassette 110 mounted in the seat 700 of the modular pump device 705. Actuation of the knob 805 to the locked state actuates a lock assembly, such as via a pair of latches 915 that latch with or otherwise engage the housing 710 to secure the door in the closed state. In the illustrated version, the knob 805 can be actuated via rotation. It should be appreciated that mechanisms other than knobs can be used as well as non-rotational actuation.

As will be described in more detail below, the actuation of the knob 805 to the locked state also automatically transitions the valve assembly of the pump cassette 110 to the "on" state to permit fluid flow through the pump cassette 110. In addition, actuation of the knob 805 to the unlocked state automatically transitions the valve assembly of the pump cassette 110, when mounted in the modular pump device 705, to the "off" state. This acts as a safeguard to ensure that the valve of the pump cassette is always closed upon removal of the pump cassette from the modular pump device and that the valve opens automatically upon being seated and secured (with the door 720 closed) in the modular pump device 700.

Figure 9:
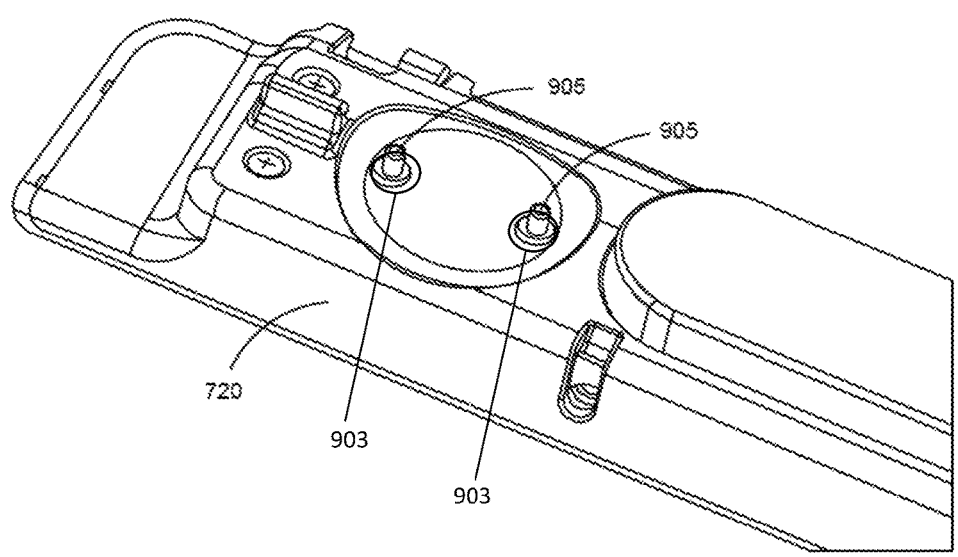
FIG. 9 shows an enlarged view of an inner portion of the door of the modular pump device.

The operation of the knob 805 and its interaction with the pump cassette 110 is now described in more detail with reference to FIG. 9, which shows an enlarged view of an inner region of the door 720 where the knob 805 is located. As mentioned, the inner portion of the door includes a pair of protrusions, such as tabs 905, that protrude toward the pump cassette 110 when the pump cassette is mounted in the seat 700 of the modular pump device 700. The tabs 905 may move inward and outward relative to the door 720. The tabs 905 may be spring-mounted via springs 903 (as schematically represented in FIG. 9) such that they are biased toward the protruded state shown in FIG. 9. In addition, the tabs 905 are positioned such that they can be aligned with and inserted into the slots 305 (FIG. 3) of the valve handle 250 when the pump cassette 110 is seated in the modular pump device and the door 720 closed. Rotation of the knob 805 (FIG. 8) results in corresponding rotation of the tabs 905. In this manner, the tabs 905 can be rotated to a position that align with and insert into the slots 305 of the valve handle 250.

For example, FIG. 7 shows the pump cassette with both the slots 305 and the tabs 905 positioned at a "12 o'clock and 6 o'clock" alignment. If the door 720 is closed, the tabs 905 will insert into and engage the slots 305 of the valve handle 250. The door 720 can then be manually or automatically closed such that the prongs insert into the slots of the valve handle 250. In this manner, the door 720 of the modular pump device physically engages the valve handle 250 via the tabs 905. Upon closing of the door, the knob 805 can be rotated to a locked position. Because the knob 805 is engaged with the valve handle 250 via the tabs 905, locking of the knob 805 rotates and actuates the valve handle 250 to the open position to permit fluid flow through the fluid lumen of the valve set. Upon unlocking of the knob 805, the knob automatically rotates the valve handle 250 back to the closed position.

The tabs 905 and slots 305 do not have to be initially aligned when the pump cassette is positioned in the seat 700 of the modular pump device 705. Rather, the valve handle 250 may be in any position (open, closed, or between the two) and the tabs 905 will automatically engage the valve handle 250 upon rotation of the knob 805. If not aligned, when the door 720 is closed the tabs 905 will just be pushed inward of the door. When the knob 805 is rotated, the tabs 905 will eventually align with the slots 305 and spring into the slots by virtue of their spring loading. In this manner, the locking of the door 720 will automatically transition the valve assembly to the on position. Likewise, unlocking of the door automatically transition the valve assembly to the off position.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores. Wireless transfer of machine language is also within the scope of this disclosure.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices, tablets, and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) when depicted in the accompanying figures and/or described herein do not necessarily require the particular order shown, or sequential order, to achieve desirable results. Other implementations may be within the scope of the following claims.

The invention claimed is:

1. A pump cassette for coupling with a pump device, the pump cassette comprising:
   a valve assembly that can be actuated to regulate fluid flow through a fluid passageway formed of a tube coupled to the cassette, the valve assembly including a valve handle that actuates to open and close a valve of the valve assembly, the valve handle including a first opening and a second opening that are positioned in a pre-aligned pattern, wherein the pre-aligned pattern of the first opening and the second opening conforms to a pre-aligned pattern of a corresponding first protrusion and second protrusion of a door of the pump device such that the first protrusion inserts into the first opening and the second protrusion inserts into the second opening of the valve handle when the first protrusion and second protrusion are aligned with the first opening and the second opening, respectively, wherein the first and second protrusions are spring biased to move toward and into the first opening and second opening when the door is closed over the pump cassette; and
   a frame coupled to the valve assembly, wherein the valve assembly is fixed on the frame prior to the frame being coupled to or inserted into the pump device, the frame adapted to be inserted into a seat of the pump device, the frame configured to be inserted into the seat only when aligned in a predetermined orientation relative to the seat wherein the frame has a flat surface juxtaposed with the fluid passageway, wherein the flat surface cooperates with a pump mechanism of the pump device such that the frame acts as a platen relative to the fluid passageway and the pump mechanism of the pump device for pumping fluid through the fluid passageway.

2. A pump cassette as in claim 1, wherein the frame has a shape that cooperates with a shape of the seat such that the frame can only be inserted into the seat when in the predetermined orientation.

3. A pump cassette as in claim 1, wherein the shape of the frame is asymmetric.

4. A pump cassette as in claim 3, wherein the shape of the frame is asymmetric about one axis.

5. A pump cassette as in claim 1, wherein the frame is shaped so as to have an enlarged, circular end region and a body region that is of smaller transverse dimension than the circular end region relative to a longitudinal axis of the frame.

6. A pump cassette as in claim 1, wherein the fluid passageway has a circular cross-sectional shape.

7. A pump cassette as in claim 1, wherein the fluid passageway has a non-circular cross-sectional shape.

8. A pump cassette as in claim 1, wherein the fluid passageway is at least partially manufactured of one of polysiloxane, plasticized polyvinyl chloride, silicone rubber, and thermoplastic elastomer.

9. A pump cassette as in claim 1, wherein the valve of the valve assembly is a rotary valve.

10. A pump cassette as in claim 1, wherein the valve includes a valve actuator that automatically engages with the door of the pump device.

11. A pump cassette as in claim 1, wherein the pump cassette is configured to provide an audible or tactile feedback upon being inserted into the seat.

12. A pump cassette as in claim 1, wherein the fluid passageway has a non-circular cross-sectional shape and further comprising a connector having a complementary shape, the connector configured to connect the fluid passageway to the tube or to the valve.

13. A pump cassette as in claim 12, wherein the connector is bonded to the fluid passageway.

14. A pump device, comprising:
   a pumping mechanism;
   a housing defining a seat configured to receive a pump cassette coupled to a fluid passageway formed of a tube that can be acted upon by the pumping mechanism so as to pump fluid through the fluid passageway of the pump cassette, wherein the pump cassette has a frame couple to a valve assembly that transitions between an open flow state that permits fluid flow through the fluid passageway and a non-flow state that blocks fluid flow through the fluid passageway, the seat shaped to receive the pump cassette only when the frame of the pump cassette is aligned in a predetermined orientation relative to the seat, and wherein the frame has a flat surface juxtaposed with the fluid passageway, wherein the flat surface cooperates with a pump mechanism of the pump device such that the frame acts as a platen relative to the fluid passageway and the pump mechanism of the pump device for pumping fluid through the fluid passageway;
   a door attached to the housing and configured to be transitioned between an open position wherein the seat is exposed for receipt of the pump cassette and a closed position wherein the door secures the pump cassette within the seat;
   a door actuator formed of a knob on the door that rotatably transitions to a locked state that locks the door in the closed position, wherein the valve assembly is fixed on the frame prior to the frame being coupled to or inserted into the seat of the housing, wherein the door actuator includes two or more tabs that protrude toward the valve assembly when the pump cassette is mounted in the seat and when the door is in the closed position, wherein the tabs are spring biased to move toward a protruded state from a non-protruded state to automatically spring into openings of a handle of the valve assembly when the door is in the closed position, the tabs being arranged in a pattern;

wherein the valve assembly of the pump cassette includes the valve handle which actuates to open and close a valve of the valve assembly, the valve handle including two or more openings that are positioned in a pattern that conforms to the pattern of the tabs such that the two or more tabs automatically insert into the two or more openings of the valve handle when the two or more tabs are aligned with the two or more openings and the door is closed over the pump cassette.

15. A pump device as in claim 14, wherein the door actuator automatically transitions the valve assembly to the non-flow state when the door actuator is transitioned to the unlocked state.

16. A pump device as in claim 14, wherein the door actuator is a rotatable knob.

* * * * *